United States Patent [19]

McGuinness et al.

[11] Patent Number: 4,775,408

[45] Date of Patent: Oct. 4, 1988

[54] PYRIDINE DERIVATIVES OF SUBSTITUTED THIADIAZOLEUREAS

[75] Inventors: James A. McGuinness, Naugatuck; John A. Minatelli, Watertown; Allyn R. Bell; Allen R. Blem, both of Cheshire, all of Conn.

[73] Assignee: Uniroyal Chemical Company, Inc., Middlebury, Conn.

[21] Appl. No.: 764,911

[22] Filed: Aug. 12, 1985

[51] Int. Cl.$^4$ ............................................. A01N 43/82
[52] U.S. Cl. ........................................ 71/90; 546/277
[58] Field of Search ............................. 71/90; 546/277

[56] References Cited

U.S. PATENT DOCUMENTS 4,518,414  5/1985  Schirmer et al. .................... 546/277
4,576,629  3/1986  Morland et al. ........................ 71/90
4,591,376  5/1986  Krähmer et al. ....................... 71/90

*Primary Examiner*—Jane T. Fan
*Attorney, Agent, or Firm*—William E. Dickheiser

[57] ABSTRACT

Pyridine derivatives of substituted thiadiazoleureas exhibit desirable herbicidal and plant growth regulatory properties.

5 Claims, No Drawings

PYRIDINE DERIVATIVES OF SUBSTITUTED THIADIAZOLEUREAS

FIELD OF THE INVENTION

This invention is directed to novel pyridine derivatives of substituted thiadiazoleureas which are useful as herbicides and as plant growth regulators. In other aspects, this invention relates to herbicidal and plant growth regulant compositions employing such novel compounds. In yet other aspects, this invention is directed to a process for preparing said thiadiazoleureas as well as to novel intermediate compounds employed in such process.

BACKGROUND OF THE INVENTION

The need for effective herbicides, both preemergence and postemergence, needs no special emphasis. The control of weeds and undesirable vegetation is of great economic importance since weed competition inhibits the production of foliage, fruits and/or seeds and may reduce the quality of the harvested crop. Weed control is essential for maximum production of many agronomic and horticultural crops including corn (*Zea mays* L.), wheat (*Triticum aestivum* L.), barley (*Hordeum vulgare* L.), oats (*Avena sativa* L.) and rice (*Oryza sativa* L.). Furthermore, weeds on noncropped areas may cause a fire hazard, undesirable drifting of sand or snow, or irritation to persons with allergies. Thus, suppression of undesirable weed growth is very advantageous.

Moreover, the need for agricultural chemicals having significant effects on the growth and development of crop plant species is similarly well known. One form of such plant growth regulation which is particularly economically important is the field of harvest aid compounds. The field of harvest aid utilization includes a wide variety of primary effects, including the defoliation of the crop plant; the desiccation of its leaves, stems, and other aerial organs; the control of late-season regrowth (e.g., for cotton); the promotion or inhibition of fruit or flower abscission; the concentration of crop maturity; and the enhancement of consumer-preferred quality factors.

Under normal conditions, many crop plants do not mature uniformly or in a timely fashion that would facilitate an efficient and optimum harvest, either due to equipment scheduling or weather considerations. Crops such as cotton, potato, sunflower, and seed legumes require either desiccation or defoliation before harvest can be effectively accomplished. Thus, for example, when cotton is not defoliated the leaves can interfere with mechanized picking apparati which are frequently employed. Also, leaves can contaminate the cotton lint with trash or green stain, which reduces the quality of the fiber or reduces the efficiency of the ginning process. Likewise, potato vines need to be desiccated for efficient mechanical digging. In addition, upon desiccation of potato leaves and stems, the tuber skin matures and becomes less susceptible to damage from the digger and postharvest handling. Seed legumes and sunflowers are also mechanically harvested, and this process is facilitated if the leaves and stems are removed or desiccated. As with cotton and potato, such defoliation or desiccation also ripens the seed uniformly, accelerates the rate of seed maturation, and conditions the pod or head for easy harvest.

Among the compounds which have been shown to exhibit herbicidal activity in the past are certain substituted thiadiazole ureas. For example, U.S. Pat. Nos. 4,066,436, 4,217,459 and 4,141,717, all issued to Kirkpatrick, disclose benzylthio-substituted thiadiazoleureas which are useful as herbicides. Somewhat similarly, U.S. Pat. Nos. 4,175,081 and 4,182,712, both issued to Driscoll, claim alkoxyalkyl and cycloalkyl-substituted thiadiazoleureas respectively, which compounds are shown to be active herbicides. Moreover, U.S. Pat. No. 4,128,412, issued to Metzger et al, shows alkyl- and arylmercapto-1,3,4-thiazol-5-yl-ureas useful as herbicides.

While the above described patents show compounds which function as herbicides, it would nonetheless be desirable to possess additional compounds which would function as herbicides, as well as compounds which would function as plant growth regulators, particularly as defoliants—the latter being a use not suggested by either the Kirkpatrick, Metzger et al or the Driscoll patents.

Accordingly, it is an object of this invention to provide novel compounds which will function admirably as herbicides and/or as plant growth regulators.

It is a further object of this invention to provide a process for the production of such novel compounds.

It is yet another object of this invention to provide novel intermediates useful in the production of said novel compounds.

It is still another object of this invention to provide herbicidal and/or plant growth regulatory compositions comprising said novel compounds.

The foregoing and additional objects will become more fully apparent from the following description and Examples.

DESCRIPTION OF THE INVENTION

In one aspect, the present invention is directed to novel pyridine derivatives of substituted thiadiazoleureas having the structural formula:

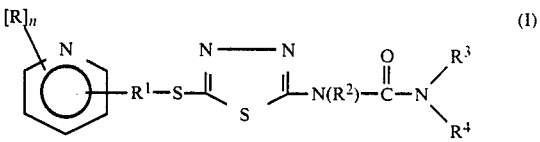

wherein:

n is 0, 1, 2, 3 or 4;

R is one or more member selected from the group consisting of:
halogen,
hydroxy,
trihalomethyl,
$OCX_aH_{3-a}$ wherein X is halogen and a=1, 2 or 3,
$SCX_aH_{3-a}$ wherein X is halogen and a=1, 2 or 3,
$C_1-C_4$ alkyl,
$C_1-C_4$ alkoxy,
$C_1-C_4$ alkylthio,
cyano,
nitro, and
$COR^5$ wherein $R^5$ is one of:
hydroxy,
$C_1-C_4$ alkoxy, or
$NR^6R^7$ wherein $R^6$ and $R^7$ are the same or different and are hydrogen or $C_1-C_4$ alkyl;

$R^1$ is $C_1-C_4$ alkylene or $C_2-C_4$ alkylidene;

$R^2$ is hydrogen or $C_1-C_4$ alkyl; and $R^3$ and $R^4$ are the same or different and are:

hydrogen, with the proviso that at least one of $R^3$ and $R^4$ is other than hydrogen,
  $C_1$–$C_4$ alkyl,
  $C_3$–$C_4$ alkenyl, or
  $C_1$–$C_4$ alkoxy, with the proviso that at least one of $R^3$ and $R^4$ is other than alkoxy;
or $R^3$ and $R^4$ taken together are
  $C_4$–$C_6$ alkylene,
  $C_4$–$C_6$ oxydialkylene, or
  $C_4$–$C_6$ azadialkylene;
with the proviso that at least one of $R^2$, $R^3$ and $R^4$ is hydrogen.

As is apparent to these skilled in the art all R substituents, and $R^1$ are bound to carbon atoms—and not to the nitrogen atom—of the pyridine ring.

This invention is also directed to agriculturally acceptable salts of such compounds, which salts are believed to involve interaction at the pyridinyl nitrogen. Illustrative of such agriculturally acceptable salts are mineral acid salts such as hydrochloride salts, hydrobromic salts and the like; carboxylic acid salts such as acetic acid salts, trichloroacetic acid salts and the like; and sulfate and sulfonate salts.

Preferably, n is 0, 1 or 2; and R is one or more member selected from the group consisting of:
  fluorine,
  chlorine,
  bromine,
  trifluoromethyl,
  methyl,
  cyano,
  nitro, and
  $COR^5$ wherein $R^5$ is OH,
    $C_1$–$C_2$ alkoxy, or
    $NH_2$;
$R^1$ is selected from the group consisting of methylene, ethylene, ethylidene, propylidene and isopropylidene;
$R^2$ is hydrogen or $C_1$–$C_2$ alkyl; and
$R^3$ and $R^4$ are the same or different and are hydrogen, $C_1$–$C_2$ alkyl or methoxy with the proviso that $R^3$ and $R^4$ are not both hydrogen or methoxy;
and hydrochloride salts thereof.

Particularly preferred compounds include:
N,N'-dimethyl-N-[5-(2-pyridinylmethyl)thio-1,3,4-thiadiazol-2-yl] urea,
N,N'-dimethyl-N-[5-(2-pyridinylmethyl)thio-1,3,4-thiadiazol-2-yl] urea hydrochloride,
N,N'-dimethyl-N-[5-(3-pyridinylmethyl)thio-1,3,4-thiadiazol-2-yl] urea,
N,N'-dimethyl-N-[5-(3-pyridinylmethyl)thio-1,3,4-thiadiazol-2-yl] urea hydrochloride,
N,N'-dimethyl-N-[5-([6-chloropyridin-2-yl]methyl)thio-1,3,4-thiadiazol-2-yl] urea,
N,N'-dimethyl-N-[5-([6-chloropyridin-2-yl]methyl)thio-1,3,4-thiadiazol-2-yl] urea hydrochloride,
N'-methyl-N-[5-([6-chloropyridin-2-yl]methyl)thio-1,3,4-thiadiazol-2-yl] urea,
N'-methyl-N-[5-([6-chloropyridin-2-yl]methyl)thio-1,3,4-thiadiazol-2-yl] urea hydrochloride,
N-methyl-N'-ethyl-N-[5-([6-chloropyridin-2-yl]methyl)thio-1,3,4-thiadiazol-2-yl] urea,
N,N'-dimethyl-N-[5-([6-fluoropyridin-2-yl]methyl)thio-1,3,4-thiadiazol-2-yl] urea,
N,N'-dimethyl-N-[5-([6-fluoropyridin-2-yl]methyl)thio-1,3,4-thiadiazol-2-yl] urea hydrochloride,
N,N'-dimethyl-N-[5-([2-fluoropyridin-4-yl]methyl)thio-1,3,4-thiadiazol-2-yl] urea,
N-methyl-N'-(2-propenyl)-N-[5-([6-fluoropyridin-2-yl]methyl)thio-1,3,4-thiadiazol-2-yl] urea, and
N-methyl-N'-(2-propenyl)-N-[5-([6-fluoropyridin-2-yl]methyl)thio-1,3,4-thiadiazol-2-yl] urea hydrochloride.

In another aspect, this invention is directed to novel intermediates of the formula:

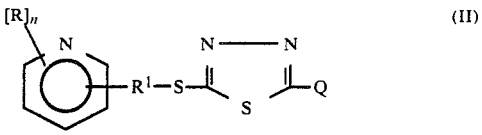

wherein R, $R^1$ and n are as defined above for formula (I); Q is $NHR^2$, NCO, or $N(R^2)COJ$ wherein $R^2$ is as defined above and J is halogen, $C_1$–$C_6$ alkoxy or phenoxy.

In general, these intermediates are prepared by a process comprising reacting a thiol of the formula:

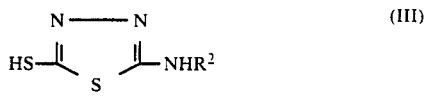

wherein $R^2$ is as defined above, with a pyridinylalkyl compound of the formula:

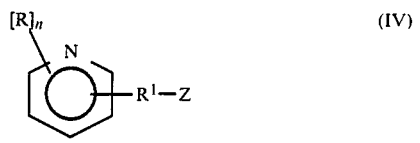

in an inert organic solvent and in the presence of an acid-binding agent. In the formula above, the symbols R, $R^1$ and n have the meanings defined above for formula (II) and Z is halogen or another suitable leaving/-displaceable group such as tosylate.

Preferably, this reaction is performed under an inert atmosphere (such as nitrogen) and in organic solvents which are miscible with water, such as ethanol, methanol, dimethylformamide and the like. The reaction temperatures may be between about 0° to about 150° C., and is preferably between room temperature and the boiling point of the reaction mixture.

The reaction time may vary from several minutes or less to several days or more, depending upon factors such as the particular reactants employed, reaction temperature, and the like. In certain instances, the use of a phase-transfer catalyst (such as tetra-n-butylammonium bromide) may be advantageous. Suitable acid-binding agents include inorganic and organic bases. Preferred acid-binding agents include alkali metal hydroxides and alkoxides. Illustrative of said preferred acid-binding agents are sodium hydroxide, potassium hydroxide, sodium methoxide, sodium ethoxide and the like.

In general, approximately equimolar amounts of the compounds of formulae (III) and (IV) and of acid-binding agent are employed in the reaction, although it is preferable that a slight excess of compound (III) and of acid-binding agent (with respect to compound (IV)) be employed.

Typically, the reaction mixture is poured into water, and a precipitated solid product is collected by filtration. However, in other instances the product is extracted from the aqueous mixture with a solvent (such as chloroform or dichloromethane) and the solvent removed in vacuo. If desired, the product can be further purified by conventional methods such as recyrstallization.

The starting compounds corresponding to structural formula (III) and (IV) are known, and are commercially available or can be readily prepared from known compounds by methods well known in the art. For example, U.S. Pat. No. 4,252,902 to Rothgery shows several processes for producing 2-(substituted)amino-5-mercapto-1,3,4-thiadiazole compounds. Several substituted picolyl chlorides are available from Aldritch (see pg. 894 of the 1984–1985 catalog), while the preparation of additional pyridinylalkyl halides are well known in the art (see, e.g., J. Org. Chem., Vol. 25, pp. 1047-8 (1960) wherein the preparation of alpha-bromo-2-ethylpyridine is described).

When Q is an amino group (i.e., NHR$^2$), the compound of formula (II) is prepared as described above. The other compounds of formula (II) may be prepared by reacting the appropriate amine compound (i.e., Q=NH$_2$) with compounds such as phosgene or N,N'-carbonyl diimidizole and the like (to produce Q=isocyanate); or with the appropriate chloroformate (to form Q=carbamate); or with phosgene with the appropriate amine (i.e., R$^2$ is other than hydrogen) (to produce Q=carbamoyl halide)—all employing known chemical processes.

The novel pyridine derivatives of substituted thiadiazoleureas of this invention are prepared by a process comprising reacting a compound of the general formula:

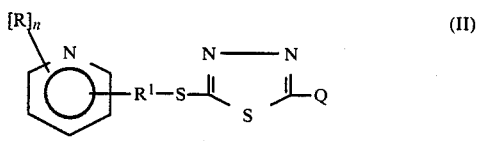

(II)

with a compound of the general formula:

R$^3$Y  (V)

wherein the symbols R, R$^1$, R$^3$ and n have the meanings defined above.

The specific composition desired will determine the particular selection of the Q and Y substituents. However, the Q and Y substituents must be selected from the following four sets of radical couples:

| (A) | Q = NHR$^2$ | and | Y = NCO; |
|---|---|---|---|
| (B) | Q = NCO | and | Y = NHR$^4$; |
| (C) | Q = NHR$^2$ | and | Y = N(R$^4$)COJ; and |
| (D) | Q = N(R$^2$)COJ | and | Y = NHR$^4$. |

In the above radicals, J is halogen (preferably chlorine), alkoxy or phenoxy, and the symbols R$^2$ and R$^4$ have the meanings defined above under the formula (I), but with the added provisos below for the particular radical couple selected.

For radical couple (A), R$^3$ cannot be hydrogen or alkoxy: for radical couple (C), R$^3$ and R$^4$ cannot be hydrogen; and for radical couple (D), R$^2$ cannot be hydrogen if J is halogen.

In procedures employing radical couples (A) or (B), an isocyanate is reacted with an amine. Typically, this reaction is conducted in a suitable inert solvent, preferably under anhydrous conditions. Such reaction maybe conducted from about 0° C. to the boiling point temperature of the reaction mixture, and is preferably conducted at from about 0° to about 70° C.

Reaction time may range from several minutes or less to several days or more, depending upon factors such as the specific reactants employed, reaction temperature, and the like. In some instances, the use of a catalyst known for enhancing amine-isocyanate reactions (such as dibutyltin diacetate, triethylamine, diazabicyclooctane (DABCO) and the like), may be advantageous.

The resultant urea product may be isolated and purified by partial removal of solvent and/or by the addition of a suitable non-solvent which will precipitate the product. Typically, the product is collected by filtration and, if necessary, may be recrystallized from convenient solvents or solvent mixtures.

In procedures employing radical couples (C) or (D), a carbamoyl halide, usually the chloride, or a carbamate (preferably phenylcarbamate) is reacted with an amine. This reaction is typically conducted in a suitable inert solvent or solvent mixture, usually in the presence of an inorganic or organic base. When an organic base is employed, preferably such base additionally functions as the solvent (e.g., when a base such as pyridine is employed).

In general, the reaction is carried out using approximately equimolar amounts of the two reactants and the base. However, the molar ratio of reactants may vary considerably, and in some cases, the use of an excess of base may be advantageous. Moreover, the use of a phasetransfer catalyst may be advantageous, especially in cases where the reaction mixture is not homogenous. Reaction temperature may vary from about 0° C. to the boiling point temperature of the reaction mixture, and is preferably between about 20° C. and about 80° C. Reaction time may vary from several minutes or less to several days or more depending upon factors such as reaction temperature, solvent, the specific reactants employed, and the like.

The starting amine compounds of radical couples (A) and (C) correspond to the compounds represented by structural formula (II), and may be prepared by the above-described method.

The starting amine compounds of radical couples (B) and (D), and the starting isocyanate compounds of radical couple (A) are known and many are commercially available.

Moreover, the starting carbamoyl halides (especially chlorides) of radical couple (C) are known and some are commercially available. The starting carbamates may be made from suitable amines and appropriate chloroformate according to known procedures.

When desired, the pyridinyl ureas represented by structural formula (I) may be converted to their corresponding agriculturally acceptable salts (i.e., pyridinium urea acid addition salt) by reacting the particular pyridinyl urea with the appropiate acid (either anhydrous or aqueous). Such reaction may employ an inert organic solvent or an aqueous solvent, and typically a reaction temperature of between about 0° and about 50° C. is employed. The resultant pyridium urea salt is then isolated and purified by known methods.

The compositions of this invention are comprised of (a) an herbicidally or plant growth regulatory effective amount of a novel pyridine derivative of a substituted thiadiazoleurea of this invention and (b) a suitable carrier. Such compositions may comprise one or more of the novel pyridine derivatives of this invention.

To prepare such agriculturally useful compositions, the pyridine derivative may be mixed with an adjuvant to provide compositions in the form of finely-divided particulate solids, granules, pellets, wettable powders, flowable liquids, soluble powders, solutions, and aqueous or organic solvent dispersions or emulsions. Such formulations may be of several different physical and chemical types, any of which could be made by one familiar with the art. For instance, the pyridine derivative may be impregnated on finely-divided or granular inorganic or organic carriers such as attapulgite clay, sand, vermiculite, corn cob, activated carbon or other granular carriers known to the art. The impregnated granules may then be spread on the soil or incorporated into the soil.

Alternatively, the chemical may be formulated as a wettable powder by grinding it into a fine powder and mixing it with an inactive powdered carrier to which a surface active dispersing agent has been added. Typical powdered solid carriers are the various mineral silicates (such as mica, talc, pyrophyllite, clays and the like) or powdered organic material (e.g., corn cob). The wettable powder may then be dispersed in water and sprayed on the soil surface, or on crop or weed plants.

Similarly, an emulsifiable concentrate may be prepared by dissolving the chemical in a solvent such as benzene, toluene, or other aliphatic or aromatic hydrocarbon to which a surface active dispersing agent generally has been added. The emulsifiable concentrate may then be dispersed in water and applied by spraying.

The concentration of active chemical in the composition may vary widely typically ranging from about 1 to about 95% by weight. The concentration of active chemical in dispersions applied to the soil, seed or foliage is typically between about 0.002% and about 80% by weight.

Formulations containing the active ingredient(s) may be dispersed in water or an organic liquid (such as oil) and applied to target plants. Surface active agents may be added to the applied solution to increase its qualitative or quantitive range of activity. Suitable surface active agents are well known to those skilled in the art. Reference may be made to McCutcheon's Detergents and Emulsifiers (1980, Allured Publ. Co., Ridgewood, NJ) for examples of appropriate surface active agents. Similarly, such formulations may be applied to the soil either as a liquid or a granule.

For use as a preemergence herbicide the compound of this invention is typically applied at a rate of from about 0.05 to about 25 pounds per acre (about 0.056 to about 28 kg/ha) to soil which contains weed and crop seed. Such application is made either to the surface of the soil or into the upper one to three inches (2.5 to 7.5 cm.) of soil. When employed as a postemergence herbicide or as a plant growth regulator the derivative is typically applied at a rate of from about 0.05 to about 25 pounds per acre (about 0.056 to about 28 kg/ha) to the aerial portions of weeds or crop plants.

The most suitable dosage of application, and the most effective type and amount of adjuvant substance will depend on a number of factors, including the plant species; the stage of plant development; the method of application; the specific biological effect desired; the air and soil temperature and the quantity and intensity of rainfall before and after treatment; the soil type, pH, fertility and moisture and organic matter content; the physiological condition and vigor of the target plants; the relative humidity and wind velocity of the air around the crop at the time of treatment; the extent and density of the foliar canopy of the target plant; the light quality, intensity and duration each day; the type and interval of previous and subsequent crop protectant chemical applications. However, one skilled in the art can, by routine experimentation, readily determine optimum conditions for the employment of any particular novel pyridine derivative.

EXAMPLES

The following Examples are intended to further illustrate the invention and are not intended to limit the scope of the invention in any manner.

EXAMPLE 1

Preparation of N-methyl-5-[(2-pyridinylmethyl)thio]-1,3,4-thiadiazol-2-amine

To a stirred mixture of 47.2 grams (0.32 mol) of 5-(methylamine)-1,3,4-thiadiazole-2(3H)-thione in 480 ml of ethanol was added 82 ml of a 25 weight percent solution of sodium methoxide (0.36 mol) in methanol. The mixture was stirred at room temperature for 15 minutes under a nitrogen atmosphere, resulting in a clear solution. To this mixture was added a slurry formed by mixing 50 grams (0.30 mol) of 2-picolyl chloride hydrochloride in 200 ml of ethanol with 74 ml of a 25 weight percent solution of sodium methoxide (0.32 mol) in methanol.

Following the initial exothermic reaction (temperature increased from 24° to 32° C.), the reaction mixture was stirred under nitrogen and heated at reflux for 3 hours.

The mixture was then cooled to room temperature, and added to 2.5 liters of an ice-water mixture. After warming to room temperature, about 200 grams of sodium chloride were added. The resulting clear solution was stirred at room temperature for 16 hours. The solution was then extracted with (4×300 ml) chloroform for each and the extract dried over anhydrous sodium sulfate. Removal of the chloroform solvent under reduced pressure yielded 67.2 grams of the title compound as an oil which on standing set to a solid, m.p. 73°–75° C.

This compound was characterized by infrared and proton nuclear magnetic resonance (NMR) spectra. The NMR spectrum was measured at 60 MHz using tetramethylsilane (TMS) as an internal standard.

The infrared and NMR spectra confirmed the structure of the compound produced.

EXAMPLE 2

Preparation of N,N'-dimethyl-N-[5-(2-pyridinyl-methyl)thio]-1,3,4-thiadiazol-2-yl] urea (Compound No.1)

To a stirred solution of 9.5 grams (0.04 mol) of N-methyl-5-[(2-pyridinylmethyl)thio]-1,3,4-thiadiazol-2-amine (prepared as in Example 1) dissolved in 150 ml of dry tetrahydrofuran and maintained at about 5° C. by the use of a cold water bath, was added 3.4 grams (0.06 mol) of methyl isocyanate. The mixture was stirred at about 5° C. for 1 hour, then 2 drops of dibutyltin diacetate catalyst were added. The mixture was allowed to warm to room temperature and was stirred overnight.

The mixture was then heated at 40° C. for 2 hours while stirring. Nitrogen was then swept over the warmed reaction mixture, thereby removing unreacted methyl isocyanate. Moreover, said heating served to concentrate the mixture. The reaction mixture was cooled to room temperature resulting in the precipitation of a solid product which was collected by vacuum filtration and dried to yield 7.6 grams of the title compound, m.p. 154°–155° C. Cooling of the filtrate gave an additional 1.5 grams of the title compound. The infrared spectrum (nujol) showed absorptions at 3340 cm$^{-1}$ (NH) and 1675 cm$^{-1}$ (urea C=O) consistent with the assigned structure. The NMR spectrum confirmed the assigned structure.

EXAMPLE 3

(a) Preparation of
5-[(3-pyridinylmethyl)thio]-1,3,4-thiadiazol-2-yl isocyanate

To a stirred mixture of 27.7 grams (0.17 mol) of N,N'-carbonyldiimidazole in 200 ml of dry tetrahydrofuran, which mixture was maintained at room temperature under a nitrogen atmosphere, was added a mixture of 17.4 grams (0.078 mol) of 5-[(3-pyridinyl-methyl)thio]-1,3,4-thiadiazol-2-amine (prepared by the method of Example 1) in 300 ml of dry tetrahydrofuran. The reaction mixture was stirred at room temperature for 1 hour and then at reflux for 15 minutes, followed by cooling to room temperature. The reaction mixture containing the title compound was used in the subsequent reaction without isolation of this isocyanate intermediate.

(b) Preparation of
N-methoxy-N-methyl-N'-[5-[(3-pyridinylmethyl)thio]1,3,4-thiadiazol-2-yl] urea (Compound No. 13)

To the stirred reaction mixture of the Example 3(a) (under a nitrogen atmosphere and cooled to 10° C.) were added 25.9 grams (0.256 mol) of triethylamine, 25 grams (0.256 mol) of O,N-dimethylhydroxylamine hydrochloride and 250 ml of dry tetrahydrofuran. The mixture was allowed to warm to room temperature and stirred for about 2 hours. Next, the mixture was added to 2 liters of an ice-water mixture. The mixture was warmed to room temperature and stirred overnight. The mixture was extracted with 750 ml of chloroform and the extract dried over anhydrous sodium sulfate. Removal of the solvent under reduced pressure yielded 16.5 grams of a crude product which was recrystallized from toluene to yield 7.9 grams of the title compound, m.p. 142.5°–144.5° C. The infrared and NMR spectra confirmed the structure assignment.

EXAMPLE 4

Preparation of
N,N'-dimethyl-N-[5-([6-fluoropyridin-2-yl]methyl)thio-1,3,4-thiadiazol-2-yl] urea hydrochloride (Compound No. 20)

Dry hydrogen chloride gas was slowly bubbled into a stirred solution of 3.0 grams (0.012 mol) of N,N'-dimethyl-N-[ 5-([6-fluorpyridin-2-yl]methyl]thio-1,3,4-thiadiazol-2-yl] urea (prepared by the method of Example 2) dissolved in a mixture of 50 ml of chloroform and 10 ml of diethyl ether over a 5 minute period at room temperature. The precipitated solid product was collected by vacuum filtration and dried to yield 3.3 grams of the title compound, m.p. 177°–179° C.

The infrared and NMR spectra confirmed the structure assignment.

In the Tables below the above compounds are summarized as well as additional chemicals made essentially in accordance with the procedures outlined above.

TABLE I

| Compound No. | n | R | R$^1$ | R$^2$ | R$^3$ | R$^4$ | m.p. °C. | Remarks |
|---|---|---|---|---|---|---|---|---|
| 1 | 0 | — | CH$_2$ | CH$_3$ | CH$_3$ | H | 154–5 | |
| 2 | 0 | — | CH$_2$ | CH$_3$ | CH$_3$ | H | 196–8* | HCl Salt |
| 7 | 0 | — | CH$_2$CH$_2$ | CH$_3$ | CH$_3$ | H | oil** | |
| 8 | 0 | — | CH$_2$ | CH$_3$ | n-C$_4$H$_9$ | H | 98–100 | |
| 9 | 0 | — | CH$_2$ | CH$_3$ | n-C$_4$H$_9$ | H | 127–130 | HCl Salt |
| 10 | 0 | — | CH$_2$ | CH$_3$ | CH$_2$CH=CH$_2$ | H | 96–7 | |
| 11 | 0 | — | CH$_2$ | CH$_3$ | CH$_2$CH=CH$_2$ | H | 146–54 | HCl Salt |
| 12 | 0 | — | CH$_2$ | H | CH$_3$ | H | 166–8 | |
| 14 | 1 | 6-Cl | CH$_2$ | CH$_3$ | CH$_3$ | H | 148–50 | |
| 15 | 1 | 6-Cl | CH$_2$ | CH$_3$ | CH$_3$ | H | 172–3 | HCl Salt |
| 16 | 1 | 6-Cl | CH$_2$ | H | CH$_3$ | H | 155–60 | |
| 17 | 1 | 6-Cl | CH$_2$ | H | CH$_3$ | H | 143–5 | HCl Salt |
| 18 | 1 | 6-Cl | CH$_2$ | CH$_3$ | C$_2$H$_5$ | H | 143–5 | |
| 19 | 1 | 6-F | CH$_2$ | CH$_3$ | CH$_3$ | H | 134–5 | |
| 20 | 1 | 6-F | CH$_2$ | CH$_3$ | CH$_3$ | H | 177–9 | HCl Salt |
| 22 | 1 | 6-F | CH$_2$ | CH$_3$ | CH$_2$CH=CH$_2$ | H | 97–100 | |
| 23 | 1 | 6-F | CH$_2$ | CH$_3$ | CH$_2$CH=CH$_2$ | H | 154–7 | HCl Salt |
| 47 | 0 | — | CHCH$_3$ | CH$_3$ | CH$_3$ | H | 114–9 | |
| 48 | 0 | — | CHCH$_3$ | H | CH$_3$ | H | 149–53 | |

*Apparent decomposition observed at melting temperature for HCl salts
**NMR spectra measured at 60 MHz in CDCl$_3$ using tetramethylsilane as an internal standard revealed: 2.85(3H,d), 3.25(2H,m); 3.65(3H,s), 4.54(2H,s); 6.75(1H,broad m), 7.0–7.4(2H,m), 7.4–7.8(1H,m); 8.45(1H,m).
wherein the numerical values of the chemical shifts (δ in ppm) are followed in parenthesis by the number of protons and a single letter indicating the character or apparent splitting pattern of the resonance at that chemical shift with s, d and m indicating singlet, doublet, and multiplet respectively.

TABLE II

[Structure: phenyl ring with [R]n, N in ring, R¹-S-C(=N-N=)-S- linked to C(=N(R²))-C(=O)-N(R³)(R⁴)]

| Compound No. | n | R | R¹ | R² | R³ | R⁴ | m.p. °C. | Remarks |
|---|---|---|---|---|---|---|---|---|
| 3 | 0 | — | CH₂ | CH₃ | CH₃ | H | 122–4 | |
| 4 | 0 | — | CH₂ | CH₃ | CH₃ | H | 195–7 | HCl Salt |
| 13 | 0 | — | CH₂ | H | CH₃ | OCH₃ | 143–5 | |

TABLE III

| Compound No. | n | R | R¹ | R² | R³ | R⁴ | m.p. °C. | Remarks |
|---|---|---|---|---|---|---|---|---|
| 5 | 0 | — | CH₂ | CH₃ | CH₃ | H | 195–7 | |
| 6 | 0 | — | CH₂ | CH₃ | CH₃ | H | 196–8 | HCl Salt |
| 21 | 1 | 2-F | CH₂ | CH₃ | CH₃ | H | 135–8 | |

Additional compounds of this invention are specifically disclosed in Table IV through VI below:

TABLE IV

| Compound No. | n | R | R¹ | R² | R³ | R⁴ |
|---|---|---|---|---|---|---|
| 24 | 1 | 6-Br | CH₂ | H | CH₃ | CH₃ |
| 25 | 2 | 5-OH, 6-I | CH₂ | CH₃ | CH₃ | H |
| 26 | 1 | 6-CN | CH₂ | nC₄H₉ | CH₃ | H |
| 28 | 1 | 6-C₄H₉ | CH₂ | CH₃ | CH₃ | H |
| 29 | 1 | 5-CONH₂ | CH₂ | CH₃ | CH₃ | H |
| 30 | 1 | 5-COOH | CH₂ | CH₃ | CH₃ | H |
| 31 | 1 | 5-COOCH₃ | CH₂ | H | CH₂CH₂CH₂CH₂ | |
| 32 | 1 | 5-COOC₄H₉ | CH₂ | H | CH₂CH₂NHCH₂CH₂ | |
| 33 | 2 | 5-OH, 6-NO₂ | CH₂ | CH₃ | CH₃ | H |
| 34 | 1 | 5-C₄H₉O | CH₂ | CH₃ | CH₃ | H |
| 35 | 1 | 4-CH₃S | CH₂ | CH₃ | CH₃ | H |
| 36 | 1 | 4-C₄H₉ | CH₂ | CH₃ | CH₃ | H |
| 37 | 1 | 5-CONHCH₃ | CH₂ | CH₃ | CH₃ | H |
| 38 | 1 | 5-CONHC₄H₉ | CH₂ | CH₃ | CH₃ | H |
| 39 | 1 | 5-CON(C₂H₅)₂ | CH₂ | CH₃ | CH₃ | H |
| 40 | 1 | 5-CF₃ | CH₂ | CH₃ | CH₃ | H |
| 41 | 1 | 6-CCl₃ | CH₂ | H | CH₂CH₂OCH₂CH₂ | |
| 42 | 1 | 6-OCH₂F | CH₂ | CH₃ | CH₃ | H |
| 43 | 1 | 6-OCHCl₂ | CH₂ | CH₃ | CH₃ | H |
| 44 | 1 | 6-SCF₃ | CH₂ | CH₃ | CH₃ | H |

TABLE V

| Compound No. | n | R | R¹ | R² | R³ | R⁴ |
|---|---|---|---|---|---|---|
| 27 | 1 | 6-CH₃ | CH₂CH₂ | CH₃ | CH₃ | CH₃ |
| 45 | 0 | — | CH₂CH₂ | CH₃ | CH₃ | H |

TABLE VI

| Compound No. | n | R | R¹ | R² | R³ | R⁴ |
|---|---|---|---|---|---|---|
| 46 | 0 | — | CH₂C(CH₃)₂ | H | OC₄H₉ | CH₃ |

Especially useful intermediates employed in the preparation of some of the compounds listed in Tables I, II and III are summarized below in Tables VII, VIII and IX respectively.

TABLE VII

| Compound No. | n | R | R¹ | Q | m.p. (°C.) |
|---|---|---|---|---|---|
| I | 0 | — | CH₂ | NH₂ | 146–8 |
| II | 0 | — | CH₂ | NHCH₃ | 73–5 |
| III | 1 | 6-Cl | CH₂ | NH₂ | 146–9 |
| IV | 1 | 6-F | CH₂ | NHCH₃ | oil* |
| V | 1 | 6-Cl | CH₂ | NHCH₃ | 95–8 |
| X | 0 | — | CH₂CH₂ | NHCH₃ | wax** |
| XI | 0 | — | CHCH₃ | NHCH₃ | oil*** |
| XII | 0 | — | CHCH₃ | NH₂ | 140–3 |

*NMR (60 MHz, CDCL₃) δ, ppm: 2.98 (3H,s), 4.29 (2H,s), 6.6–7.0 (1H,m), 7.0–7.5 (2H,m), 7.5–8.0 (1H,m).

**NMR (60 MHz, CDCl₃) δ, ppm: 2.86 (3H,d), 3.30 (2H,m), 4.55 (2H,m), 6.2–6.8 (1H,m), 7.0–7.4 (2H,m), 7.4–7.9 (1H,m), 8.4–8.7 (1H,m).

***NMR (60 MHz, CDCl₃) δ, ppm: 1.71 (3H,d), 2.91 (3H,s), 4.63 (1H,q), 6.9–7.7 (4H,m), 8.34 (1H,m).

TABLE VIII

| Compound No. | n | R | R¹ | Q | m.p. (°C.) |
|---|---|---|---|---|---|
| VI | 0 | — | CH₂ | NH₂ | 118–21 |
| VII | 0 | — | CH₂ | NHCH₃ | 88–90 |

TABLE IX

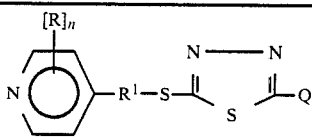

| Compound No. | n | R | R¹ | Q | m.p. (°C.) |
|---|---|---|---|---|---|
| VIII | 0 | — | $CH_2$ | $CH_3$ | oil* |
| IX | 1 | 2-F | $CH_2$ | $CH_3$ | oil** |

*NMR (60 MHz, CDCl₃) δ, ppm: 2.93 (3H,s), 4.16 (2H,s), 6.8–7.4 (3H,m), 8.2–8.5 (2H,m).
**NMR (60 MHz, CDCl₃) δ, ppm: 3.02 (3H,s), 4.30 (2H,s), 6.9–7.7 (3H,m), 7.7–8.5 (1H,m).

EXAMPLE 5

Preemergence Control

To illustrate the effectiveness of the novel pyridine derivative compounds of this invention as preemergence herbicides, 300 mg of each of the below listed compounds were dissolved in 10 ml acetone to which 30 mg of an emulsifying agent, ethoxylated sorbitan monolaurate, were added. The solution was diluted to 100 ml with distilled water. Ten milliliters of this 3000 ppm solution were diluted to 250 ppm with distilled water. The chemical was applied at the rate of 10 lb/A (11.2 kg/ha) by drenching 46 ml of the 250 ppm solution on the surface of soil in 4½ inch (11.25 cm.) plastic pots wherein seeds of the following weeds had been planted; velvetleaf (*Abutilon theophrasti* Medic.) (VL), jimsonweed (*Datura stramonium* L.) (JW), tall morninglory (*Ipomea purpurea* L. Roth)(TM), switchgrass (*Panicum virgatum* L.) (SG), barnyard grass (*Echinochloa crusgalli* (L.) Beauv.) (BG), green foxtail (*Setaria viridis* (L.) Beauv.) (GF). The percent control of the weeds compared to untreated checks was determined two weeks after treatment. Table X summarizes the results achieved with compounds formulated as indicated above, and the data clearly indicate the good to excellent herbicidal efficacy of compounds of this invention.

TABLE X

| | Preemergence Control, % at 11.2 kg/ha | | | | | |
|---|---|---|---|---|---|---|
| Cpd. No. | VL | JM | TM | GB | SG | GF |
| 1 | 100 | 0 | 0 | 75 | 60 | 80 |
| 3 | 100 | 0 | 0 | 0 | 0 | 0 |
| 9 | 0 | 0 | 0 | 25 | 100 | 100 |
| 14 | 100 | 25 | 40 | 50 | 25 | 100 |
| 15 | 100 | 0 | 100 | 100 | 20 | 60 |
| 18 | 0 | 0 | 0 | 25 | 0 | 100 |
| 19 | 100 | 0 | 100 | 70 | 0 | 100 |
| 20 | 100 | 15 | 50 | 85 | 100 | 100 |
| 21 | 100 | 0 | 100 | 95 | 0 | 100 |
| 22 | 75 | 0 | 0 | 25 | 0 | 100 |

EXAMPLE 6

Postemergence Control

To illustrate the effectiveness of the compounds of this invention as postemergence herbicides, the 3000 ppm solution described under Example 5 was atomized with a conventional DeVilbiss [trademark] sprayer, wetting the foliage to the drip point. Similarly, compounds applied at the rate of 6000 ppm were formulated by dissolving 600 mg chemical in 10 ml acetone. The remainder of the procedure was the same as described under Example 5. The weeds, which were the same species as described under Example 5, were treated six days after emergence. The percent weed control was evaluated two weeks after treatment. Table XI discloses the results.

TABLE XI

| | Postemergence Control, % at 3000 ppm | | | | | |
|---|---|---|---|---|---|---|
| Cpd. No. | VL | JM | TM | BG | SG | GF |
| 1 | 100 | 0 | 100 | 100 | 0 | 35* |
| 2 | 100 | 55 | 100 | 100 | 90 | 100* |
| 3 | 100 | 85 | 100 | 100 | 95 | 75* |
| 4 | 100 | 0 | 100 | 100 | 95 | 100* |
| 5 | 100 | 0 | 75 | 35 | 0 | 0* |
| 6 | 100 | 75 | 100 | 100 | 95 | 85* |
| 7 | 100 | 10 | 100 | 95 | 75 | 100 |
| 8 | 0 | 0 | 0 | 5 | 0 | 0 |
| 9 | 100 | 0 | 50 | 95 | 20 | 100 |
| 10 | 0 | 0 | 75 | 10 | 0 | 25 |
| 11 | 100 | 0 | 100 | 100 | 80 | 100 |
| 12 | 100 | 15 | 85 | 100 | 100 | 100 |
| 13 | 90 | 0 | 95 | 15 | 0 | 75 |
| 14 | 100 | 50 | 100 | 100 | 100 | 100 |
| 15 | 100 | 80 | 100 | 100 | 100 | 100 |
| 16 | 100 | 0 | 100 | 100 | 100 | 100 |
| 17 | 100 | 0 | 100 | 100 | 100 | 100 |
| 18 | 100 | 75 | 100 | 100 | 100 | 100 |
| 19 | 100 | 0 | 100 | 100 | 100 | 100 |
| 20 | 100 | 75 | 100 | 90 | 100 | 100 |
| 21 | 100 | 80 | 90 | 95 | 100 | 100 |
| 22 | 100 | 15 | 100 | 100 | 100 | 100 |
| 23 | 100 | 40 | 100 | 100 | 100 | 100 |

Remarks:
*tested at 6000 ppm

EXAMPLE 7

Cotton Defoliation

Suspensions of compounds of this invention were prepared at a concentration of 1500 parts per million (ppm) by dissolving 75 mg of each compound in 5 ml acetone and then adding distilled water containing 2000 ppm surface active agent [(ethoxylated sorbitan monolaurate) Tween [trademark] 20] to a total volume of 50 ml. Four cotton plants (*Gossypium hirsutum* L. cv. Stoneville 213) having leaves at three to four nodes were treated with the above indicated suspension by immersing the lower leaves in such suspensions. The plants were then removed from the suspensions and placed in a greenhouse, and after two weeks the treated plants were inspected for abscission of the treated leaves. The results are indicated in Table XII.

EXAMPLE 8

Crop Plant Dessication

To illustrate the effectiveness of the described pyridine derivatives of 1,3,4-thiadiazole ureas as crop plant desiccants, a 3000 ppm solution/suspension of active ingredient was made up in a manner similar to that described in Example 6. Those chemical solutions/suspensions were applied to soybean (*Glycine max* (L.) Merr. cv. Williams) and cotton (*Gossypium hirsutum* L. cv. Stoneville 213) plants by atomization with a Devilbiss [trademark] Model 152 sprayer, wetting the foliage to the drip point.

After 3 weeks in the greenhouse, the plants were scored for leaf desiccation on a 0 to 100 scale, 0 being no damage and 100 being complete kill. A rating system suggested by Frans and Talbert (Research Methods in Weed Science, 2nd Edition, Southern Weed Science Society (1977)) was used as a guide. The desiccation scores for both species were summed (200 =complete kill of both species), and the data obtained also appear in Table XII.

Similar pesticidal results are obtained using the compounds Nos. 24 through 46.

TABLE XII

| Cpd. No. | Cotton Defoliation, % at 1500 ppm | Combined Soybean and Cotton Desiccation at 3000 ppm |
|---|---|---|
| 1 | 100 | 200 |
| 2 | 100 | 200 |
| 3 | 100 | 200 |
| 4 | 100 | 200 |
| 5 | 100 | 25 |
| 6 | 100 | 200 |
| 7 | 100 | 200 |
| 8 | 13 | 20 |
| 9 | 0 | 80 |
| 10 | 50 | 80 |
| 11 | 38 | 120 |
| 12 | 100 | 180 |
| 13 | 63 | 130 |
| 14 | 100 | 200 |
| 15 | 100 | 200 |
| 16 | 100 | 200 |
| 17 | 100 | 200 |
| 18 | 100 | 200 |
| 19 | 100 | 200 |
| 20 | 100 | 200 |
| 21 | 100 | 200 |
| 22 | 92 | 185 |
| 23 | 100 | 195 |

The data show the good to excellent efficacy of the compounds of this invention as plant growth regulators.

EXAMPLE 9

In order to compare the effectiveness of the novel pyridine derivatives of this invention to known compounds, a series of comparative tests relating to the effectiveness of the compounds as cotton defoliants and preemergence and postemergence pesticides was run as described above, against prior art compounds N,N'-dimethyl-N-[5-([3-fluorophenyl]methyl)thio-1,3,4-thiadiazol-2-yl]urea and N,N'-dimethyl-N-[5-([3-chlorophenyl]methyl)thio-1,3,4-thiadiazol-2-yl]urea, disclosed in U.S. Pat. No. 4,141,171 to Kirkpatrick. When tested as a postemergent herbicide the pyridine derivatives show superior activity against barngrass as compared to the 3-chlorophenyl compound, the 3-fluorophenyl compound not having been tested. The results of the cotton defoliation and preemergent testing are shown in Tables XIII and XIV below:

TABLE XIII

Cotton Defoliation

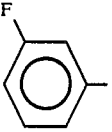

| R | Percent Defoliation at (in ppm) | | |
|---|---|---|---|
|   | 100 | 25 | 6 |
| F-phenyl | 100 | 83 | 0 |

TABLE XIII-continued

Cotton Defoliation

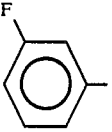

| R | Percent Defoliation at (in ppm) | | |
|---|---|---|---|
|   | 100 | 25 | 6 |
| F-pyridyl | 100 | 100 | 17 |
| Cl-phenyl | 100 | 100 | 92 |
| Cl-pyridyl | 100 | 100 | 100 |

TABLE XIV

Preemergent Herbicidal Activity
(Percent control at 11.2 kg/ha)

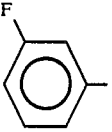

| R | VL | JM | TM | BG | SG | GF |
|---|---|---|---|---|---|---|
| F-phenyl | NOT TESTED | | | | | |
| F-pyridyl | 100 | 0 | 100 | 70 | 0 | 100 |
| Cl-phenyl | 0 | 0 | 0 | 0 | 0 | 0 |
| Cl-pyridyl | 100 | 25 | 40 | 50 | 25 | 100 |

The above data indicate the unexpectedly superior herbicidal and plant growth regulatory effect of several of the compounds of this invention relative to a prior art benzylthio-substituted analog.

What is claimed is:

1. A method for aiding in the harvesting of crops comprising postemergently applying to such crops an effective amount of a composition comprising:
(a) a compound having the structural formula:

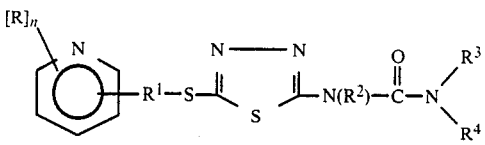

wherein:
n is 0, 1, 2, 3 or 4;
R is one or more member selected from the group consisting of:
halogen,
hydroxy,
trihalomethyl,
$OCX_aH_{3-a}$ wherein X is halogen and a=1, 2 or 3,
$SCX_aH_{3-a}$ wherein X is halogen and a=1, 2 or 3,
$C_1$-$C_4$ alkyl,
$C_1$-$C_4$ alkoxy,
$C_1$-$C_4$ alkylthio,
cyano, and
nitro, and
$COR^5$ wherein $R^5$ is one of;
hydroxy,
$C_1$-$C_4$ alkoxy, or
$NR^6R^7$ wherein $R^6$ and $R^7$ are the same or different and are hydrogen or $C_1$-$C_4$ alkyl;
$R^1$ is $C_1$-$C_4$ alkylene or $C_2$-$C_4$ alkylidene;
$R^2$ is hydrogen or $C_1$-$C_4$ alkyl; and
$R^3$ and $R^4$ are the same or different and are;
hydrogen, with the proviso that at least one of $R^3$ and $R^4$ is other than hydrogen,
$C_1$-$C_4$ alkyl,
$C_3$-$C_4$ alkenyl, or
$C_1$-$C_4$ alkoxy, with the proviso that at least one of $R^3$ and $R^4$ is other than alkoxy;
with the proviso that at least one of $R^2$, $R^3$ and $R^4$ is hydrogen; agriculturally acceptable salt thereof; and
(b) a suitable carrier.

2. The method of claim 1 wherein:
n is 0, 1 or 2; and
R is one or more member selected from the group consisting of:
fluorine,
chlorine,
bromine,
trifluoromethyl,
methyl,
cyano,
nitro, and
$COR^5$ wherein $R^5$ is
OH
$C_1$-$C_2$ alkoxy, or
$NH_2$;
$R^1$ is selected from the group consisting of methylene, ethylene, ethylidene, propylidene and isopropylidene;
$R^2$ is hydrogen or $C_1$-$C_2$ alkyl; and
$R^3$ and $R^4$ are the same or different and are hydrogen, $C_1$-$C_2$ alkyl or methoxy with the proviso that $R^3$ and $R^4$ are not both hydrogen or methoxy;
or the hydrochloride salt thereof.

3. The method of claim 1 wherein compound (a) is at least one member selected from the group consisting of:
N,N'-dimethyl-N-[5-(2-pyridinylmethyl)thio-1,3,4-thiadiazol-2-yl]urea,
N,N'-dimethyl-N-[5-(2-pyridinylmethyl)thio-1,3,4-thiadiazol-2-yl]urea hydrochloride,
N,N'-dimethyl-N-[5-(3-pyridinylmethyl)thio-1,3,4-thiadiazol-2-yl]urea,
N,N'-dimethyl-N-[5-(3-pyridinylmethyl)thio-1,3,4-thiadiazol-2-yl]urea hydrochloride,
N,N'-dimethyl-N-[5-([6-chloropyridin-2-yl]methyl)thio-1,3,4-thiadiazol-2-yl]urea,
N,N'-dimethyl-N-[5-([6-chloropyridin-2-yl]methyl)thio-1,3,4-thiadiazol-2-yl]urea hydrochloride,
N'-methyl-N-[5([6-chloropyridin-2-yl]methyl)thio-1,3,4-thiadiazol-2-yl]urea,
N'-methyl-N-[5-([6-chloropyridin-2-yl]methyl)thio-1,3,4-thiadiazol-2-yl]urea hydrochloride,
N-methyl-N'-ethyl-N-[5-([6-chloropyridin-2-yl]methyl)thio-1,3,4-thiadiazol-2-yl]urea,
N,N'-dimethyl-N-[5-([6-fluoropyridin-2-yl]methyl)thio-1,3,4-thiadiazol-2-yl]urea,
N,N'-dimethyl-N-[5-([6-fluoropyridin-2-yl]methyl)thio-1,3,4-thiadiazol-2-yl]urea hydrochloride,
N,N'-dimethyl-N-[5-([2-fluoropyridin-4-yl]methyl)thio-1,3,4-thiadiazol-2-yl]urea,
N'-methyl-N'-(2-propenyl)-N-[5-([6-fluoropyridin-2-yl]methyl)thio-1,3,4-thiadiazol-2-yl]urea, and
N'-methyl-N'-(2-propenyl)-N-[5-([6-fluoropyridin-2-yl]methyl)thio-1,3,4-thiadiazol-2-yl]urea hydrochloride.

4. A method in accordance with claim 1 wherein said crops are selected from the group consisting of cotton, soybeans and potatoes.

5. A method in accordance with claim 1 wherein such harvesting aid involves the defoliation of crops.

* * * * *